United States Patent [19]

Murad et al.

[11] Patent Number: 5,571,846
[45] Date of Patent: *Nov. 5, 1996

[54] METHOD OF INHIBITING FIBROSIS

[75] Inventors: Saood Murad; Sheldon R. Pinnell, both of Durham, N.C.

[73] Assignee: Duke University, Durham, N.C.

[ * ] Notice: The term of this patent shall not extend beyond the expiration date of Pat. No. 5,374,660.

[21] Appl. No.: 351,484

[22] Filed: Dec. 7, 1994

Related U.S. Application Data

[63] Continuation of Ser. No. 17,795, Feb. 16, 1993, Pat. No. 5,374,660, which is a continuation of Ser. No. 678,472, Apr. 1, 1991, abandoned.

[51] Int. Cl.$^6$ .................................................. A61K 31/165
[52] U.S. Cl. ............................................................. 514/620
[58] Field of Search ..................................... 514/358, 620, 514/851

[56] References Cited

U.S. PATENT DOCUMENTS

| | | | |
|---|---|---|---|
| 4,321,273 | 3/1982 | Ishikawa et al. | 424/78.17 |
| 4,382,941 | 5/1983 | Sicardi | 514/358 |
| 4,916,149 | 4/1990 | Palosi et al. | 514/387 |
| 5,374,660 | 12/1994 | Murad et al. | 514/620 |

FOREIGN PATENT DOCUMENTS

| | | |
|---|---|---|
| 51-19135 | 2/1976 | Japan . |
| 828344 | 2/1960 | United Kingdom . |

OTHER PUBLICATIONS

*Remington's Pharmaceutical Sciences* 425 (A. Gennaro Ed. 18th Ed. 1990).

A. Hayasaka et al; Serum concentrations of the carboxyterminal cross–linking domain of procollagen type IV (NC1) and the aminoterminal propetide of procollagen type III (PIIIP) in chronic liver disease, *Journal of Hepatology* 10 pp. 17–22 (1990).

M. Artico, et al; Inhibition of Copper–Dependent Amine Oxidases by Some Hydrazides of Pyrrol–1–ylbenzoic and Pyrrol–1–ylpehnylacetic Acids, *Journal of Medicinal Chemistry* 31 No. 4, pp. 802–806 (1988).

L. Morpurgo, et al; Spectroscopic studies of the reaction between bovine serum amine oxides (copper–containing) and some hydrazides and hydrazines, *Biochem. J.* 256, 565–570 (1988).

M. J. Carrington, et al; The inhibition of lysyl oxidase in vivo by isoniazid and its reversal by pyridoxal, *Biochem. J.* 221, pp. 837–843 (1984).

J. O. Gordeladze, et al; A Simple Procedure for the Determination of Hydroxyproline in Urine and Bone, *Biochemical Medicine* 20, pp. 23–30 (1978).

I. Bergman and R. Loxley; Two Improved and Simplified Methods for the Spectrophotometric Determination of Hydroxyproline, *Analytical Chemistry* 35, No. 12, pp. 1962–1965 (1963).

A. Burger; *Medicinal Chemistry* 2nd Ed. pp. 78–80 (1960).

*Primary Examiner*—Kevin E. Weddington
*Attorney, Agent, or Firm*—Bell, Seltzer, Park & Gibson

[57] ABSTRACT

Disclosed is a method of inhibiting fibrosis in a human or animal subject afflicted with a fibrosing disorder. The method comprises administering to the subject an effective fibrosis-inhibiting amount of a compound of Formula (I):

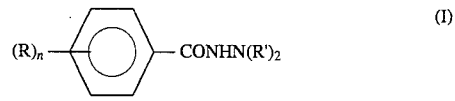

wherein:
  n is 1 or 2;
  R is selected from the group consisting of hydrogen, C1–C4 alkyl, hydroxy, amino, and nitro; and
  R' is selected from the group consisting of hydrogen and C1–C4 alkyl.
  or a pharmaceutically acceptable salt thereof. Preferred as a compound of Formula (I) is benzoic hydrazide. Pharmaceutical formulations and the use of compounds of Formula (I) for making the same are also disclosed.

9 Claims, 4 Drawing Sheets

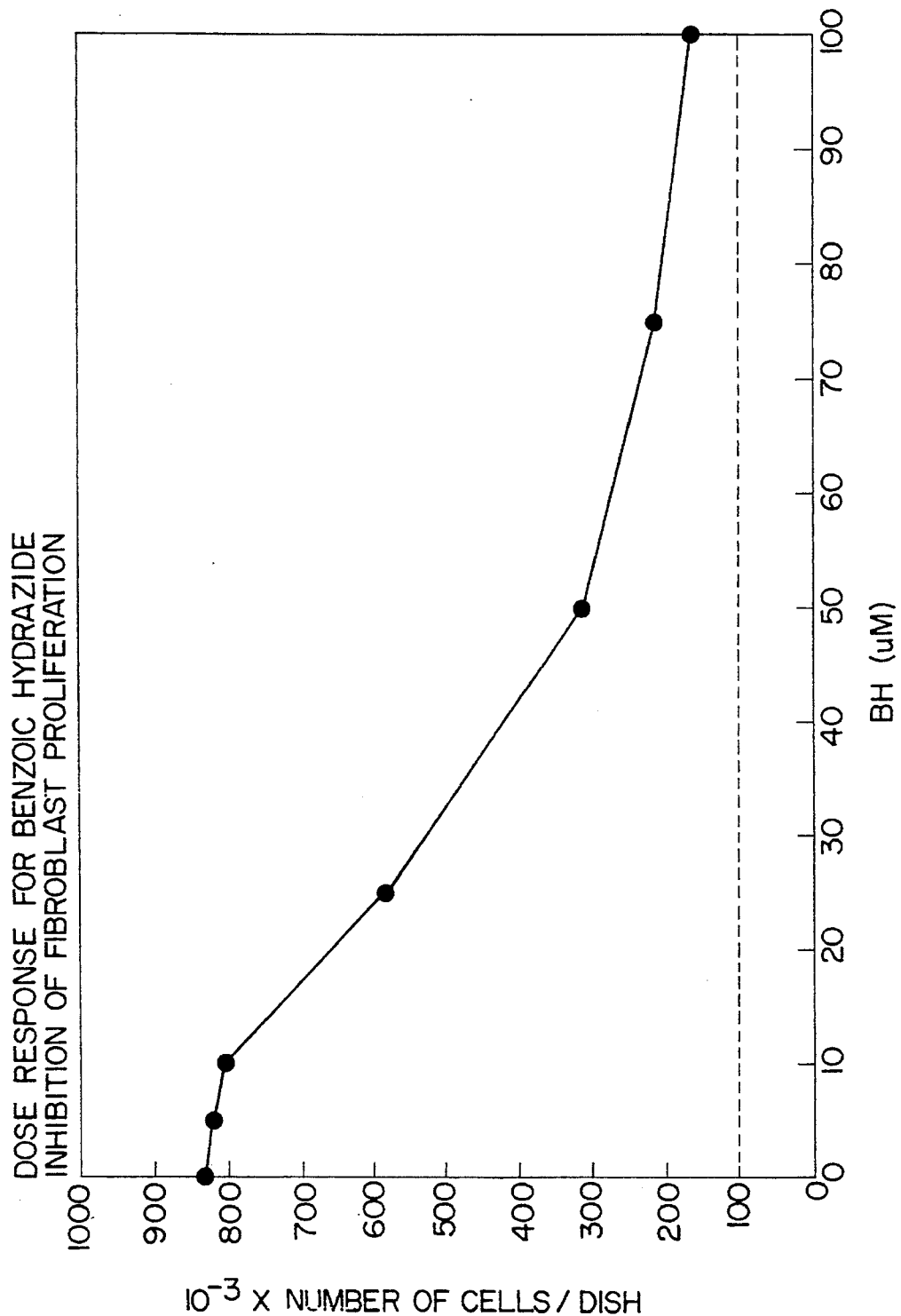

METHOD OF INHIBITING FIBROSIS

This invention was made with Government support under Grant Nos. 5R37 AR17128 and 5ROI AR28304 from the National institutes of Health. The Government may have certain rights to this invention.

This application is a continuation of application Ser. No. 08/017,795 filed Feb. 16, 1993, now U.S. Pat. No. 5,374,660, which is a continuation of application Ser. No. 07/678,472, filed Apr. 1, 1991, now abandoned, the disclosure of which is incorporated by reference herein in its entirety.

FIELD OF THE INVENTION

The present invention relates to methods and compositions for inhibiting fibrosis and combating fibrosing disorders in subjects in need of such treatment.

BACKGROUND OF THE INVENTION

Fibroblasts are the major cell type responsible for the synthesis of collagen, a fibrous protein essential for maintaining the integrity of the extracellular matrix found in the dermis of the skin and other connective tissues. The production of collagen is a finely regulated process, and its disturbance may lead to the development of tissue fibrosis. The formation of fibrous tissue is part of the normal beneficial process of healing after injury. However, in some circumstances there is an abnormal accumulation of fibrous material such that it interferes with the normal function of the affected tissue.

Central to the development of fibrotic conditions, whether spontaneous or induced, is stimulation of fibroblast activity. Many common debilitating diseases, such as liver cirrhosis and pulmonary fibrosis, involve the proliferation of fibrous tissue as do certain skin diseases such as scleroderma, keloids, and hypertrophic scars.

Excessive accumulation of collagen in the extracellular matrix, resulting from exuberant fibroblast proliferation and/or collagen production, is a major biochemical abnormality in the fibrosis of a number of tissues including the skin. Attempts to control the abnormal accumulation of collagen have focused on several inhibitors of the translational and post-translational reactions in collagen biosynthesis, but their therapeutic value is limited by certain undesirable features, i.e., poor permeability across cell membrane, nonspecificity in action, or toxicity. There is, accordingly, a continuing need for new antifibrotic agents.

SUMMARY OF THE INVENTION

We have identified a hydrazine derivative, benzoic hydrazide, which appears to be free from the limitations inherent in previous antifibrotic agents and offers the potential to be a powerful antifibrotic agent by virtue of its ability to suppress the synthesis of collagen as well as the proliferation of fibroblasts in culture causing further reduction in the amount of collagen produced. The present invention accordingly provides a method of inhibiting fibrosis in a subject afflicted with a fibrosing disorder. The method comprises administering to the subject an effective fibrosis-inhibiting amount of a compound of Formula (I):

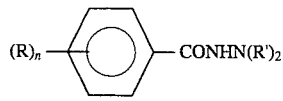

(I)

wherein:

n is 1 or 2, preferably 1;
R is selected from the group consisting of hydrogen, C1–C4 alkyl, hydroxy, amino, and nitro; and
R' is selected from the group consisting of hydrogen and C1–C4 alkyl, preferably hydrogen.
or a pharmaceutically acceptable salt thereof.

A second aspect of the present invention is a pharmaceutical formulation comprising a compound according to Formula I above, or a pharmaceutically acceptable salt thereof, in an effective fibrosis-combating amount, in a pharmaceutically acceptable carrier.

A third aspect of the present invention is the use of a compound of Formula (I) above, or a pharmaceutically acceptable salt thereof, for the manufacture of a medicament for combating a fibrosing disorder.

BRIEF DESCRIPTION OF THE INVENTION

FIG. 4 shows the dose response for benzoic hydrazide inhibition of fibroblast proliferation. Benzoic hydrazide concentration in microMollar is given on the horizontal axis, and $10^{-3}$ times the number of cells per dish is given on the vertical axis.

DETAILED DESCRIPTION OF THE INVENTION

Figure 1:
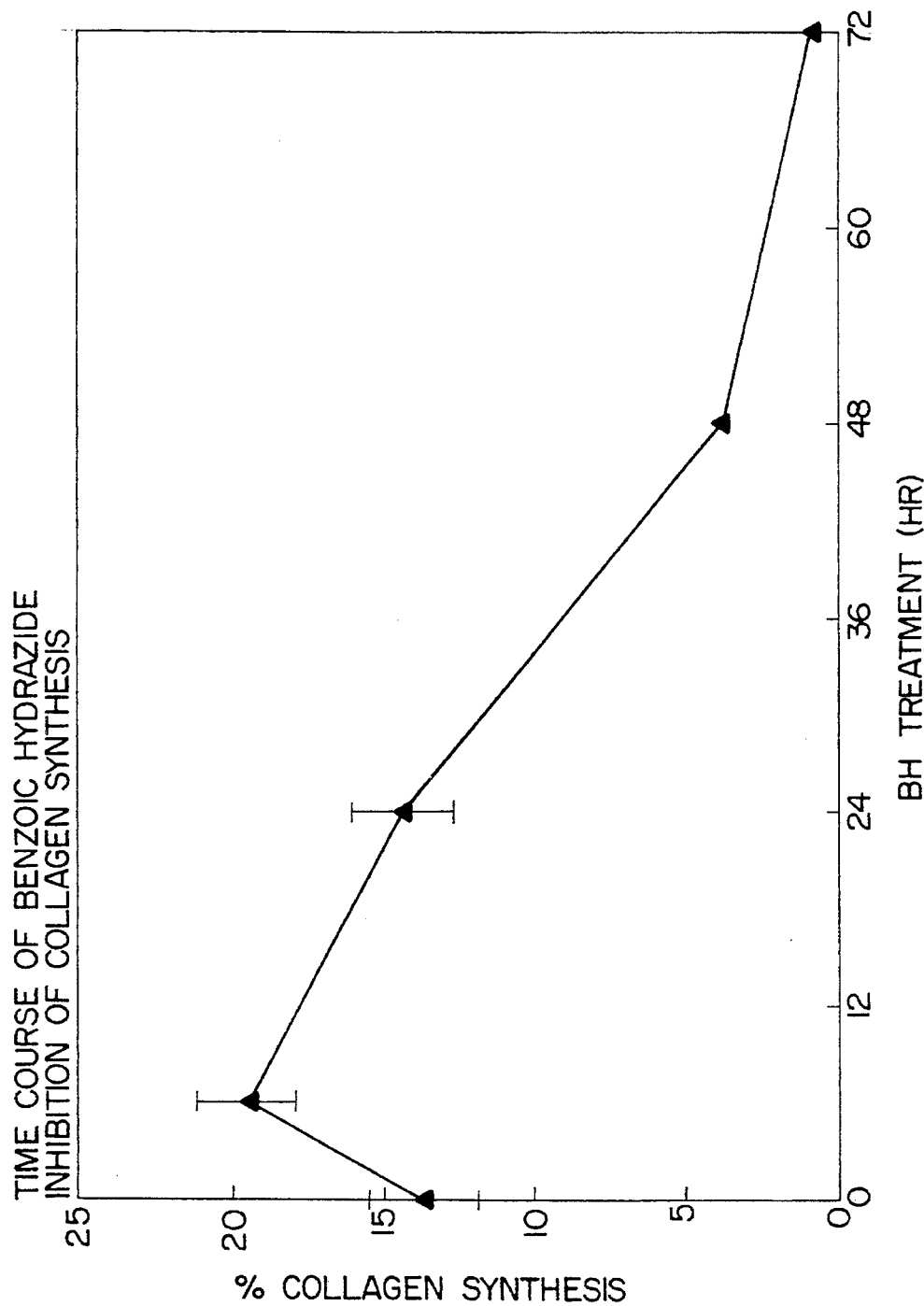
FIG. 1 shows the time course of benzoic hydrazide inhibition of collagen synthesis. The duration of benzoic hydrazide treatment in hours is given on the horizontal axis and the percent of collagen synthesis is given on the vertical axis.

Compounds illustrative of Formula (I) above include, but are not limited to, benzoic hydrazide, 2-nitrobenzoic hydrazide, 2-aminobenzoic hydrazide, 4-nitrobenzoic hydrazide, 4-aminobenzoic hydrazide, 4-hydroxybenzoic hydrazide, 3-nitrobenzoic hydrazide, 3-aminobenzoic hydrazide, 3-hydroxybenzoic hydrazide, 3,5-dihydroxybenzoic hydrazide, 2,4-diaminobenzoic hydrazide, 3,4-diaminobenzoic hydrazide, and 3,4-dinitrobenzoic hydrazide. Currently preferred is benzoic hydrazide ($C_6H_5CONHNH_2$). Such compounds may be prepared by procedures known to those skilled in the art. The term "alkyl" as used herein refers to, for example, methyl, ethyl, propyl, and butyl. Note that dihydroxy substitutions adjacent one another on the ring of the compound of Formula (I) (e.g., ortho dihydroxy such as hydroxy substitutions at the 3 and 4 positions) or a monohydroxy substitution adjacent the carbonyl group (e.g., hydroxy at the 2 postion) result in compounds which are metal chelators and are accordingly less desireable.

Subjects to be treated by the method of the present invention include, but are not limited to, subjects afflicted with a dermal fibrosing disorder, subjects afflicted with fibrosis of an internal organ, and subjects afflicted with fibrotic conditions of the eye.

Dermal fibrosing disorders include, but are not limited to, scleroderma, morphea, keloids, hypertrophic scars, familial cutaneous collagenoma, and connective tissue nevi of the collagen type. Such disorders are preferably treated by administering the compound of Formula (I) topically.

Fibrosis of internal organs (e.g., liver, lung, kidney, heart blood vessels, gastrointestinal tract), occurs in disorders such as pulmonary fibrosis liver cirrhosis, and scar formation. Such disorders are preferably treated by administering the compound of Formula (I) parenterally or orally.

Fibrotic conditions of the eye include conditions such as diabetic retinopathy, postsurgical scarring (for example, after glaucoma filtering surgery and after cross-eye surgery), and proliferative vitreoretinopathy, which may be treated by the topical application to they eye of an opthalmic formulation containing a compound of Formula (I).

Subjects to be treated by the method of the present invention include both human and animal (e.g., dog, cat, cow, horse) subjects.

The compound of Formula (I) may be administered in a total amount per day of not more than about 50 mg/kg body weight, more preferably not more than about 25 mg/kg, and most preferably not more than about 10 mg/kg. With respect to minimum dose, the compound of Formula (I) is preferably administered in a total amount per day of at least about 0.01 mg/kg, more preferably at least about 0.1 mg/kg, and most preferably at least about 1 mg/kg. The compound may be administered once or several times a day. When prepared as a formulation for topical administration the formulation may contain from about 0.1 percent to about 10 percent by weight of the active ingredient.

As noted above, the compounds of Formula (I) may be administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts.

The present invention also provides pharmaceutical formulations, both for veterinary and for human medical use, which comprise the compound of Formula (I) together with one or more pharmaceutically acceptable carriers thereof (and optionally any other therapeutic ingredients). The carrier(s) must be pharmaceutically acceptable in the sense of being compatible with the other ingredients of the formulation and not unduly deleterious to the recipient thereof.

The formulations of the present invention include those suitable for topical, ophthalmic, parenteral (including subcutaneous, intramuscular and intravenous), oral, nasal, and rectal administration. Formulations suitable for topical and parenteral administration are preferred.

The formulations may conveniently be presented in unit dosage form and may be prepared by any of the methods well known in the art of pharmacy. All methods include the step of bringing the active compound into association with a carrier, which carrier constitutes one or more accessory ingredients. In general, the formulations are prepared by uniformly and intimately bringing the active compound into association with a liquid carrier, a finely divided solid carrier, or both, and then, if necessary, shaping the product into desired formulations.

Topical formulations comprise the active compound dissolved or suspended in one or more media such as mineral oil, petroleum, polyhydroxy alcohols or other bases used for topical pharmaceutical formulations. The addition of other accessory ingredients may also be desirable.

Formulations suitable for parenteral administration conveniently comprise a sterile aqueous preparation of the active compound, such as sterile pyrogen-free water or saline solution, which is preferably isotonic with the blood of the recipient subject.

Ophthalmic formulations comprise purified aqueous solutions of the compound of Formula (I) with preservative agents and isotonic agents. The formulations are preferably adjusted so that the pH and isotonic factors match that of the eye.

Formulations of the present invention suitable for oral administration may be presented as discrete units such as capsules, cachets, tablets or lozenges, each containing a predetermined amount of the compound of Formula (I) as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following Examples are provided to illustrate the present invention, and should not be construed as limiting thereof. In these examples, mm means millimeters; mM means milliMolar; ml means milliliters; SD means standard deviation; μM means microMolar; cpm means counts per minute; M means Molar; and temperatures are given in degrees Centigrade.

EXAMPLE 1

Effect of Various Compounds Including Benzoic Hydrazide on Collagen Synthesis

Cultures grown to confluence in 35 mm dishes were incubated for 72 hours in medium supplemented with 0.5% dialyzed calf serum. The cultures received 1 mM of test compound for the entire duration of 72 hours. Cultures were labeled during the last six hours with 20 μci of L-[2,3-$^3$H]-proline in 1 ml of medium. The amount of radioactivity incorporated into collagen in the medium and cells combined was measured after digestion with a bacterial collagenase and is expressed as the percentage of radioactivity incorporated into total collagen plus noncollagen proteins, corrected for the relative abundance of proline in collagen. Data are given in Table 1 below. Note the uniquely high activity of benzoic hydrazide as compared to the other compounds tested.

TABLE 1

Effects of Various Compounds Including Benzoic Hydrazide on Collagen Synthesis

| Treatment[a] | Relative Collagen Synthesis[b] (% of Control) |
| --- | --- |
| Control | 100 |
| Benzoic hydrazide | 19 |
| Phenylacetic hydrazide | 88 |
| Acetic hydrazide | 92 |
| Isonicotinic hydrazide | 88 |
| Nicotinic hydrazide | 108 |
| Biotin hydrazide | 107 |
| Benzamide | 110 |
| Ethyl benzoate | 99 |

[a]72 hours, 1 mM
[b]In two cultures analyzed in duplicate, SD were within 14%

EXAMPLE 2

Time Course for Benzoic Hydrazide Inhibition of Collagen Synthesis

This Example was conducted in essentially the same manner as Example 1 above, except that the cultures received a fixed dosage of 1 mM benzoic hydrazide for the entire 72 hour duration of incubation or the last 48, 24, 6 or 0 hours of incubation. Data are given in FIG. 1. Note the time-dependent effect on collagen synthesis caused by benzoic hydrazide.

EXAMPLE 3

Dose Response for Benzoic Hydrazide Inhibition of Collagen Synthesis

Figure 2:
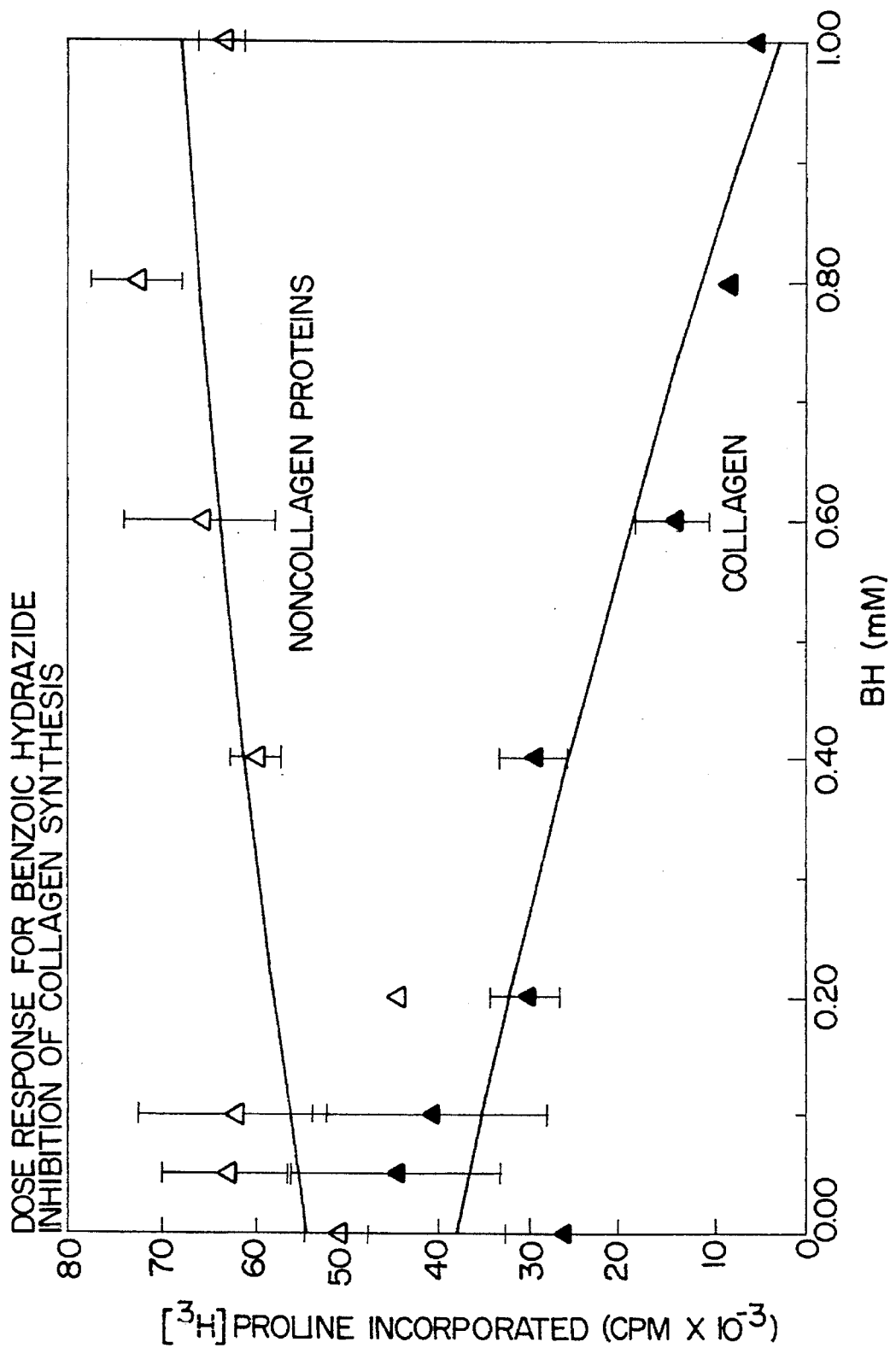
FIG. 2 shows the dose response for benzoic hydrazide inhibition of collagen synthesis. Benzoic hydrazide concentration in milliMolar is given on the horizontal axis, and the amount of [$^3$H]Proline incorporated in cpm times $10^{-3}$ is given on the vertical axis.

This Example was conducted in essentially the same manner as Example 1 above, except that cultures were incubated for a fixed time of 72 hours with varying concentrations of benzoic hydrazide ranging from 0.00 to 1.00 mM. Data are shown in FIG. 2. Note the lack of effect on noncollagen proteins, as well as the dose-dependent effect on collagen synthesis caused by benzoic hydrazide.

EXAMPLE 4

Effect of Benzoic Hydrazide on Procollagen Secretion

This Example was conducted in essentially the same manner as Example 1 above, except that cells were incubated with either 1 mM Benzoic hydrazide, 100 μM Ascorbate, or both for 72 hours. Data are given in Table 2 below. Note the reduction in procollagen secretion caused by benzoic hydrazide.

TABLE 2

Effect of Benzoic Hydrazide on Procollagen Secretion

| Treatment[a] | Radioactivity in Collagen | | Percent Secretion[d] |
| --- | --- | --- | --- |
| | Medium cpm/10$^6$ | Cell Layer cells | |
| Control | 2965 ± 126 | 9533 ± 774 | 24 |
| Benzoic hydrazide[b] | 80 ± 0 | 1578 ± 162 | 5 |
| Ascorbate[c] | 17953 ± 1968 | 2448 ± 17 | 88 |
| Ascorbate[c] + Benzoic Hydrazide | 279 ± 115 | 1416 ± 341 | 16 |

[a]72 hours
[b]1 mM
[c]100 μM
[d]Expressed as the ratio of radioactivity in collagen in the medium relative to that in the medium plus cell layer, times 100

EXAMPLE 4

Effect of Benzoic Hydrazide on Prolyl Hydroxylation

Confluent cultures were treated for 72 hours with 1 mM benzoic hydrazide and labeled during the last 24 hours with 12.5 μCi of L-[2,3-$^3$H]-proline per ml of medium. The collagenous proteins from the medium and cells were separately extracted, reduced with dithiothreitol (DDT), and electrophoretically analyzed on 4–15% sodium dodecyl sulfate-polyacrylamide gels. The bands corresponding to the proα1(I) and proα2(I) chains from the two fractions were pooled and hydrolyzed with 6M HCl for 24 hours at 110° C. Proline and hydroxyproline in the hydrolysate were separated by high performance liquid chromatography and quantitated by liquid scintillation counting. Data are given in Table 3 below. Note that the procollagen synthesized by benzoic hydrazide-treated fibroblasts was deficient in hydroxyproline, compared to proline.

TABLE 3

Effect of Benzoic Hydrazide on Hydroxylation of Proline Residues in Procollagen

| Treatment[a] | Hydroxyproline cpm | Proline | Percent Hydroxylation[d] |
| --- | --- | --- | --- |
| Control | 1566 | 4800 | 25 |
| Benzoic hydrazide[b] | 194 | 4493 | 4 |
| Ascorbate[c] | 3836 | 3218 | 54 |
| Ascorbate[c] + Benzoic hydrazide[b] | 1345 | 6000 | 18 |

[a]72 hours
[b]1 mM
[c]100 μM
[d]Expressed as the ratio of radioactivity in hydroxyproline to hydroxyproline plus proline, times 100

EXAMPLE 5

Effect of Benzoic Hydrazide on Levels of Procollagen and Fibronectin mRNAs

Figure 3:
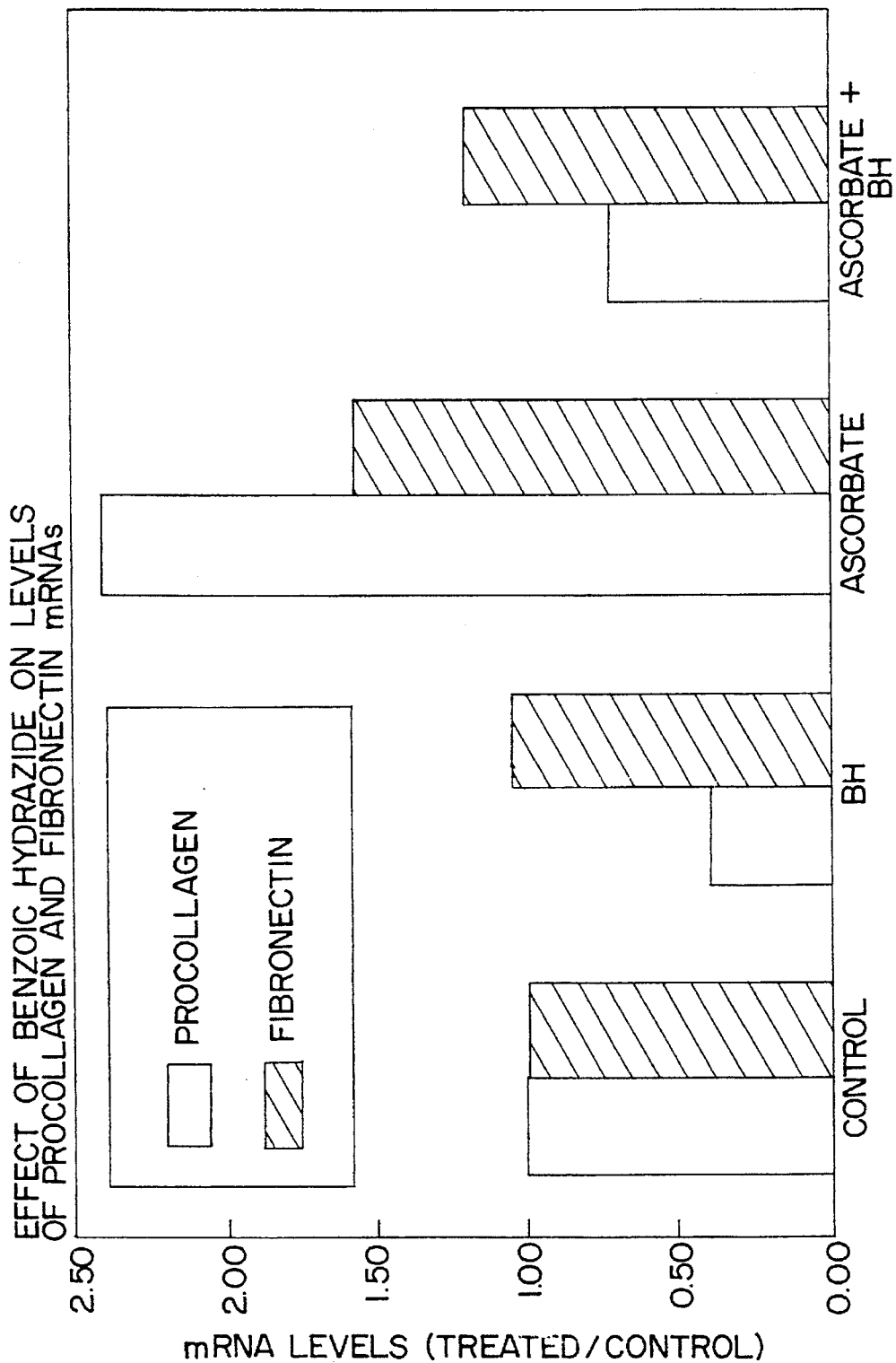
FIG. 3 shows the effect of benzoic hydrazide on levels of procollagen and fibronectin mRNAs in, from left to right, control, benzoic hydrazide, ascorbate, and ascorbate plus benzoic hydrazide treated cultures. mRNA levels (treated/control) are given on the vertical axis. Procollagen levels are shown in the open columns and fibronectin levels are shown in the filled columns.

Total RNA isolated from cultures treated as above was analyzed by Northern blot hybridization to [$^{32}$P]-labeled fibronectin and proα1(I) collagen cDNAs. The blots corresponding to fibronectin and proα1(I) collagen mRNAs were visualized by autoradiography and quantitated by densitometric scanning. Data are given in FIG. 3. Note that the inhibition of collagen synthesis by benzoic hydrazide was associated with a specific reduction in the level of procollagen mRNA.

EXAMPLE 6

Dose Response for Benzoic Hydrazide Inhibition of Fibroblast Proliferation

Cultures of human skin fibroblasts (100,000 cells) were placed into 60 mm dishes containing Dulbecco's modified Eagle's medium supplemented with 20% calf serum. The cultures were incubated at 37° C. in a humidified atmosphere of 5% $CO_2$/95% air. One day after plating, cultures were treated with 0.00 to 100 µM benzoic hydrazide. Seven days after plating, cells were harvested by trypsinization, and an aliquot of cell suspension was counted in a Coulter counter to determine the number of cells. Data are given in FIG. 4. Note the dose-dependent effect on fibroblast proliferation caused by benzoic hydrazide.

The foregoing examples are illustrative of the present invention, and not to be construed as limiting thereof. The invention is defined by the following claims, with equivalents of the claims to be included therein.

That which is claimed is:

1. A method of inhibiting fibrosis in a subject afflicted with a fibrosing disorder, comprising administering to said subject an effective fibrosis-inhibiting amount of a compound of Formula (I)

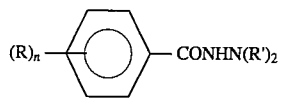

wherein:

n is 1 or 2;

R is selected from the group consisting of hydrogen, C1–C4 alkyl, hydroxy, amino, and nitro; and R' is selected from the group consisting of hydrogen and C1–C4 alkyl;

or a pharmaceutically acceptable salt thereof.

2. A method according to claim 1, wherein n is 1.

3. A method according to claim 1, wherein R' is hydrogen.

4. A method according to claim 1, wherein said compound is selected from the group consisting of 2-nitrobenzoic hydrazide, 4-nitrobenzoic hydrazide, 4-aminobenzoic hydrazide, and 4-hydroxybenzoic hydrazide.

5. A method according to claim 1, wherein said subject is afflicted with a dermal fibrosing disorder.

6. A method according to claim 1, wherein said subject is afflicted with fibrosis of an internal organ.

7. A method according to claim 1, wherein said subject is afflicted with a fibrotic condition of the eye.

8. A method according to claim 1, wherein said compound is administered topically.

9. A method according to claim 1, wherein said compound is administered parenterally.

* * * * *